United States Patent [19]

Juengst, Jr. et al.

[11] 4,333,956
[45] Jun. 8, 1982

[54] CALCIUM AMMONIUM LACTATE AND SOLIDIFIED FERMENTED AMMONIATED CONDENSED WHEY

[75] Inventors: Fred W. Juengst, Jr., Green Bay; John A. Dika, Kewaunee, both of Wis.

[73] Assignee: Calor Agriculture Research, Inc., Okemos, Mich.

[21] Appl. No.: 109,480

[22] Filed: Jan. 4, 1980

Related U.S. Application Data

[63] Continuation-in-part of Ser. No. 93,162, Nov. 13, 1979, abandoned.

[51] Int. Cl.$^3$ .............................................. A23K 1/08
[52] U.S. Cl. ........................................ 426/69; 426/74; 426/512; 426/515; 426/516; 426/583; 426/623; 426/626; 426/630; 426/635; 426/807
[58] Field of Search ................. 426/69, 512, 2, 74, 426/41, 42, 623, 630, 635, 636, 515, 516, 520, 807, 583, 626

[56] References Cited

U.S. PATENT DOCUMENTS

2,904,437  9/1959  Czarnetzky .................... 426/41 X
4,160,041  7/1979  Schroeder et al. ............. 426/807 X

OTHER PUBLICATIONS

Hanula et al., "Powdered Feed from Corn" Chemical Abstracts, 1976, vol. 84, Abstract No. 149585m.
Webb, "Byproducts from Milk", Avi Publishing Co., (1970), pp. 59-61.

*Primary Examiner*—R. B. Penland
*Attorney, Agent, or Firm*—Cushman, Darby & Cushman

[57] ABSTRACT

Fermented ammoniated condensed whey (FACW) is solidified by mixing it with certain calcium salts and allowing the mixture to stand. The mixture, while still liquid, may be mixed with grains, roughage and forage materials, or it may be shaped into blocks, cubes or pellets. Solidified FACW can be used as a feed supplement for ruminant animals. During the solidification calcium ammonium lactate is formed which is a new crystalline chemical composition. Calcium ammonium lactate (CAL) may be prepared in purified form from lactic acid, calcium hydroxide and ammonia. CAL is useful independently as a feed supplement for ruminant animals.

14 Claims, No Drawings

CALCIUM AMMONIUM LACTATE AND SOLIDIFIED FERMENTED AMMONIATED CONDENSED WHEY

This is a continuation-in-part of prior United States application Ser. No. 93,162, filed Nov. 13, 1979, now abandoned.

The present invention relates to solidified forms of fermented ammoniated condensed whey (hereinafter called "FACW") and methods of making same. The invention is also related to calcium ammonium lactate, a constituent formed in that method which assists in solidification of FACW and which is a useful nutrient for ruminant animals.

BACKGROUND OF THE INVENTION

FACW is a liquid feed supplement which is manufactured by fermenting whey with lactic acid producing bacteria, such as *Lactobacillus bulgaricus*, in the presence of ammonia. The fermentation of whey converts carbohydrate to lactic acid, which is neutralized by ammonia to form ammonium lactate. The fermentation also multiplies the bacteria, which consequently provide additional protein. The fermentation product, which typically will contain 6 to 16% solid matter, is then concentrated by evaporation typically to a solids content of 40 to 68%.

Since ruminant animals can utilize ammonium salts as a source of nitrogen for synthesis of protein, FACW is useful as a feed supplement for them. As a liquid, it can be applied to other ration components, such as shelled corn silage, oats, or oil seed meals. It would be useful, however, to have FACW available in a solid form, for example, for use on farms which are not equipped to use liquid feed supplements.

Protein supplement and mineral blocks, pellets or other feeds processed via binding are normally made with expensive presses using binders such as molasses, lignin sulfonate or bentonite. These methods often require steam conditioning of the meal prior to pressing and the application of high pressure (2000 to 3000 psi). The current invention, while compatible with this equipment, is a basic improvement in that this equipment is not necessary and little or no pressure or heat need be applied to form blocks. This invention offers considerable savings of time, energy and capital over current practices.

SUMMARY OF THE INVENTION

In accordance with the present invention, FACW or other liquid substances containing similar concentrations of ammonium lactate and total solids can be solidified by mixing it with certain calcium salts. Depending on the salt used and the conditions of addition, substantial amounts of heat can be generated. At elevated temperatures the FACW or ammonium lactate-containing substance can be maintained as a liquid. The rate of solidification in turn can be regulated by controlling the rate and extent of cooling. For example, with calcium chloride, the mixture typically begins to thicken at 25° to 30° C. and can solidify completely within an hour. The solidified product reaches maximum hardness after one to several days. This hardening is not associated with evaporation of water, since it will occur in an air-tight package.

The invention is applicable to the manufacture of solid FACW in various forms. In its raw form, it can be solidified in molds to form lick blocks or cubes, or it can be extruded to produce pellets or granules. The solidified material can be crushed to form a powder or it can be "shaved" to produce flakes.

Trace ingredients such as minerals, vitamins or drugs can also be added to the FACW prior to processing. Substantial amounts of molasses, corn steep liquid or other feed ingredient also may be added.

In accordance with the invention the aforesaid compositions may be used to make animal feed products in which they bind products such as grains, roughage and forage materials into blocks, cubes or pellets. The compositions serve as excellent binding agents when blended in liquid form with those products and permitted to solidify. Typically such mixtures will contain 20 to 40% FACW and 1 to 3% added calcium. Prior to solidification the mixtures can be poured and/or compressed into range blocks or cubes or extruded to form pellets. The compressed mass can then harden in twenty minutes or less. Unlike conventional binders these compositions are believed to serve to "cement" the solid product particles rather than serving as a simple "adhesive". For this reason the application of excessive pressure is not required to achieve solidification.

MECHANISM OF SOLIDIFICATION

As previously described, FACW contains ammonium lactate as a primary constituent. It can exist as a solid, but since it is highly hydroscopic it remains liquefied under normal atmospheric conditions. The mechanism by which FACW is solidified by the invention is not fully understood. However, it is believed to involve the formation of calcium ammonium lactate dihydrate (CAL), a solid crystalline substance. As presently understood, solvated calcium combines chemically with the ammonium lactate in FACW, resulting in the production of the CAL salt which crystallizes and/or precipitates in mass to effect total solidification.

It has been found that in some cases, calcium ammonium lactate forms as a byproduct in the manufacture of FACW. The CAL sometimes deposits in manufacturing equipment as a sediment, for example in pipes or storage vessels. This deposition can be prevented by removing calcium from the whey used to make FACW. Such removal can be accomplished by ion exchange, prior to fermentation. A suitable ion exchange system is the resin Amberlite 200. Conversely, CAL can be obtained by purification of FACW, i.e., by separating CAL crystals from FACW to obtain substantially pure CAL.

Calcium ammonium lactate salt (CAL) has been synthesized in the laboratory in the following manner: 500 parts by volume of the solution in lactic acid is neutralized with 257 parts of aqueous ammonia (27.7% $NH_3$) and 5.55 parts by weight of $Ca(OH)_2$ or (1.1 parts $CaCl_2.2H_2O$). The mixture is cooled to room temperature, pH adjusted to 6.8 with 1.0 NaOH solution and diluted to 1 liter with water. After standing 4 to 7 days, well-formed crystals will form usually, however, seeding with CAL crystals and agitation may be necessary. The total crystal yield is approximately 5% by weight of the prepared solution.

The chemical composition of the resulting salt is as follows:

| Constituent | Percent[1] |
| --- | --- |
| Calcium | 8.6 |
| Ammonia Nitrogen as $NH_4$ | 7.7 |

-continued

| Constituent | Percent[1] |
| --- | --- |
| Lactic Acid expressed as $C_3H_5O_3$ | 74.4 |
| Water | 11.1 |
| Total | 102.8 |

[1] Average of 6 determinations.

The empirical formula of the compound based on the above analytical data is $Ca(NH_4)_2 (C_3H_5O_3)_4 \cdot 2H_2O$. Unequivocal confirmation of this empirical formula has not been made.

The crystalline solid is characterized by monolithic symmetry. The compound does not have a distinct melting point, but appears to lose waters of hydration at 120° C. and decompose at 190°±5° C. CAL is very soluble in water, slightly soluble in aqueous ammonia and insoluble in ethanol. The solid has a specific gravity of 1.47.

Calcium ammonia lactate is useful in its own right as a feed supplement for ruminant animals. CAL contains approximately 37.4 percent by mass of crude protein equivalent and the lactic acid constituent can serve as a valuable source of metabolizable energy. Calcium is an essential mineral of great nutritional importance. All of the constituents contained are valuable sources of animal nutrition making CAL a concentrated feed supplement that contains total feed value.

DETAILED DESCRIPTION

The present invention is applicable to FACW obtainable from various types of whey and having a variety of compositions. FACW contains, as specified in section #573.450 of the Federal Register, 35 to 55% ammonium lactate.

The calcium salts which are used in accordance with the invention are salts of strong mineral acids, such as calcium chloride, calcium sulfate and calcium phosphate. Calcium chloride is preferred, being effective in smaller quantities, and producing harder products, than calcium sulfate, which in turn is more effective than calcium phosphate. Effectiveness is believed to be correlated with water solubility. It is possible also to use alkaline calcium salts such as calcium carbonate, calcium oxide or calcium hydroxide. However, when alkaline calcium salts are used, a mineral acid must be added in an amount sufficient to neutralize, so that the FACW is not rendered alkaline, so as to prevent loss of ammonia. Preferably sufficient mineral acid is added to form the calcium salt with all of the calcium.

The amount of calcium required to solidify an FACW-containing feed to any specified hardness generally has to be determined experimentally. It has been found that 6 to 10% calcium, by weight of FACW, is generally sufficient. This amount is the percentage of calcium. The amount of any particular calcium salt must be adjusted to give the appropriate amount of calcium.

The most elementary application of this invention is the solidification of FACW. The FACW and calcium salt are mixed at room temperature to dissolve the salt and the mixture poured into a suitable mold for hardening. It is best to slowly add this salt while vigorously mixing FACW to eliminate clumping and hasten its solution. If an alkaline calcium salt is used in combination with mineral acids, as described above, the acids are best added to the FACW during agitation followed by the slow addition of the alkaline salt. If calcium chloride ($CaCl_2 \cdot 2H_2O$) is used singly or if mineral acids are added prior to the addition of an alkaline salt, extensive heat is generated. Calcium chloride has a positive heat of solution and typically produces a temperature rise of 1° to 1.5° C. (2° to 3° F.) for each percent of the dihydrate added. When mineral acids are used in combination with alkaline calcium salts, the heats generated result primarily from the solution of the acids. The neutralization of the acidified FACW by the alkaline salt is not significantly exothermic. A rise of 1.5° C. (3° F.) is typically observed for each percent of mineral acid (95% $H_2SO_4$ or 85% $H_3PO_4$) added.

The FACW-calcium mixture can be maintained as a free flowing liquid if the temperature is maintained above the temperature at which solidification is spontaneously initiated. This critical temperature is typically 25° to 30° C. but can vary depending on the exact composition of the FACW, the calcium salt used, the amount of calcium added and the rate of cooling. If the FACW prior to calcium addition is at room temperature (20° C.), the elevated temperature obtained following typical additions of calcium chloride or mineral acids plus alkaline salts is sufficiently high to maintain the FACW-calcium mixture in a liquid state. For example, if an FACW-calcium mixture is to contain 20% by mass of the dihydrate, with a temperature of 20° C. prior to blending, the temperature of the mixture will be typically 40° to 50° C. following complete solution of the calcium salts. Such a mixture will remain as a liquid for a prolonged period, unless it is cooled. If the additions do not result in a mixture having a temperature that is greater than the critical solidification temperature, sufficient heat must be applied to the FACW fraction before blending to prevent premature solidification.

By regulating the rate and extent of cooling, the rate of solidification can be controlled. Relatively rapid solidification can result if the fluid is cooled at a specified rate to a temperature that nearly equals or is slightly lower (supercooling) than the critical temperature before being poured into a mold. Once the critical temperature is attained, the product can be maintained as a liquid for a period of approximately 2 to 5 minutes, which is sufficient time to transfer the slightly thickened fluid from the mixing vessel to the solidification mold. Once solidification is initiated, a hard, dry product can result in about 15 minutes or less. The exact rate and extent of cooling employed when applying this method must be determined experimentally and will vary with the formulation used and the FACW composition. It is necessary to control the rate of cooling so as to permit mold pouring at the critical temperature or during the supercooling phase. If cooling is too rapid, solidification can result prematurely and the method cannot be applied to attain the desired result.

Rapid solidification is desired when insoluble materials such as minerals or grain fragments are slurried or suspended in liquid FACW prior to initiating the solidification process. When the process is controlled to produce rapid solidification the suspended material can be homogeneously distributed in the finished solid. This process is especially applicable to the production of lick blocks containing insoluble matter where the matter must be homogeneously suspended.

If the FACW mixture to be solidified contains no suspended solid matter, it may be desirable to implement a slow-setting procedure. This procedure is simpler to employ, since careful regulation of the cooling rate is not necessary. The FACW-calcium mixture is simply maintained at a temperature that is greater than the solidification temperature, poured into an appropriate mold and permitted to cool (usually under ambient conditions) until the solidification temperature is attained and solidification is achieved. With this method, solidification usually occurs in from 1 to 6 hours depending on the formulation used, the initial temperature of the fluid and the cooling conditions. Generally the temperature at which the fluid is poured should be at least 2° to 5° C. above the known solidification temperature so as to avoid premature solidification that could occur if pouring were attempted at a slightly lower temperature. If the temperature is more than 5° C. above the known solidification temperature, solidification will be delayed.

In addition to the production of solidified FACW in molds, this invention can be applied to the production of FACW pellets or cubes using commonly known extrusion type devices. To apply these devices to liquid FACW-calcium mixtures at elevated temperatures, the mixtures must be cooled to the point at which solidification is initiated (or supercooled) and forced through the extrusion device precisely when the desired consistency is attained. When using such a process, the rate and extent of cooling have to be carefully regulated so that the material is thickened to a desirable consistency just prior to being forced through the die of the extrusion device. After it has been formed, the extruded material can harden completely within minutes. The exact timing must be determined by trial for each formulation used.

FACW solidification in accordance with the invention can be conducted also with the inclusion of other nutrients, such as molasses, corn steep liquid, yeast extract products, minerals and vitamins. In addition, drugs added to feed products may be included depending on the final use of the product. For example, Rumensin ® could be added to blocks, pellets or cubes for feeding cattle. In general, larger amounts of calcium salt are needed to attain a desired hardness when the FACW contains excessive amounts of molasses than when the process is practiced with FACW itself. Mixtures containing up to 25 parts by weight of molasses for each 100 parts of FACW may be solidified using conventional amounts of the calcium salts. Higher levels than 25 parts of molasses may be used, but the level of calcium may have to be elevated. Other ingredients may also influence solidification, and trial and error must be implemented to determine the level of calcium required to effect hardening.

A more sophisticated application of this invention is the use of FACW-calcium mixtures to bind forage, roughage and other plant products when producing protein-concentrate pellets, cubes or range-blocks. It is best to premix the FACW and calcium salt maintaining the temperature high enough to prevent premature solidification, blend the resulting mixture with the ruminant animal feeds again maintaining an elevated temperature, and compress the blend in a mold or apply extrusion-type processing. In such products it is generally desirable to include about 30 to 40% by weight of the FACW-calcium salt mixture. The exact amounts of FACW and calcium required for solidification will vary with the nature of the ingredients included in the formulation, and the desired hardness of the block. The exact formulation must be determined experimentally for each intended binding application.

When feeds of this type are produced using FACW, the regulation of temperature during production is critical to the success of the process. Solidification of the FACW fraction must be prevented until the feed mixture is fully blended and compacted or extruded to its final shape by maintaining it above the solidification temperature. If solidification is premature, the ingredients will not bind adequately.

Generally if the liquid FACW-calcium premix and the plant ingredients are blended rapidly and compressed or processed immediately, a well bound product will result, even without auxiliary heating. Generally, when the liquid FACW-calcium mixture is at 40°-50° C., and it is blended in normal proportions with the plant product mixture at room temperature, the temperature of the resulting blend is low enough to initiate solidification of the FACW-calcium fraction. However, the mixture generally will remain sufficiently moist and sticky to permit good compaction to occur for a period of approximately 5 to 10 minutes. If the blended feed is to remain for an extended period of time before compression processing, the total feed must be heated so as to maintain it above the solidification temperature.

After blending the FACW, calcium salt and plant ingredients, the mixture is compressed in the desired form and left to harden by the solidification of the FACW. During formation sufficient pressing must be applied to compact the product to a convenient density, i.e., remove extraneous pockets of air. If the solidified product is not to cure or be stored in a mold, sufficient pressure must be applied to maintain the shape of the product until solidification is sufficiently complete to allow the shape to be maintained before the product is removed from the mold.

The following examples illustrate the invention. All parts and percentages are given on a weight basis, unless stated otherwise.

EXAMPLE I

The following formulation was used to produce a 30-pound lick-type range block:

| Ingredient | Percent |
|---|---|
| FACW (60% solids) | 80 |
| CaCl$_2$ . 2H$_2$O | 20 |
| | 100 |

A 5-gallon bucket was used as a mixing vessel, with agitation from an air-driven barrel mixer fitted with a single set of three 2-inch blades. The mixing vessel was placed within a 15-gallon tub which was filled with water for rapid cooling of the blended feed ingredients. The mold used to shape the lick block was a 3-gallon plastic tub (6 × 11 × 14 inches). Utilization of the plastic tub permitted easy removal of the finished block, since the inside walls were smooth and slightly tapered at the open end.

The CaCl$_2$.2H$_2$O fraction (6 pounds) was poured slowly into the vigorously mixing FACW fraction (24 pounds). The mixture was agitated for approximately 5 minutes to assure complete solution of the added salt. After mixing, the temperature of the FACW mixture was elevated 33° C. from room temperature to approximately 56° C. After the initial 5 minutes of mixing, cold tap water was circulated through the cooling vessel and the fluid cooled at an approximate rate of 1.5°±0.5° C.

per minute. The fluid mixture began to thicken when a temperature of approximately 31° C. was reached, and it was immediately poured into the mold for solidification. The mixture hardened in about 10 minutes and was removed from the mold after 1 hour. The block attained maximum hardness after two or three days of curing.

The finished block was chemically analyzed and observed to contain the following:

| Constituent | Percent (M/M) |
|---|---|
| CPE | 36.9 |
| CPE from non-protein nitrogen | 31.6 |
| Lactic acid | 29.8 |
| Estimated solids | 68.0 |
| Calcium | 5.85 |

This block was fed free-choice to a herd of heifers and dry cows under normal field conditions and was observed to provide adequate palatability and weatherability.

EXAMPLE II

A 30-pound lick-type block similar to that of Example I was prepared with the inclusion of black strap molasses from the following formulation:

| Ingredient | Percent |
|---|---|
| FACW (60% solids) | 70 |
| $CaCl_2 \cdot 2H_2O$ | 20 |
| Molasses, Black Strap | 10 |
| | 100 |

The procedure used to produce this block was similar to that employed in Example I. The FACW and molasses were premixed, then the calcium salt was added as previously described. This material required approximately six hours to solidify and several days to attain maximum hardness.

The finished block was chemically analyzed and observed to contain the following:

| Constituent | Percent |
|---|---|
| CPE | 33.3 |
| CPE from non-protein nitrogen | 28.4 |
| Lactic acid | 27.9 |
| Estimated solids | 69.5 |
| Calcium | 5.78 |

This block when used in the field as a lick-feed was palatable and weathered well.

EXAMPLE III

The following formulation was used to produce a 30-pound FACW range block using calcium carbonate plus acids for solidification:

| Ingredients | Percent |
|---|---|
| FACW (60% solids) | 68 |
| $CaCO_3$ | 15 |
| 85% $H_3PO_4$ | 15 |
| 95% $H_2SO_4$ | 2 |
| | 100 |

In addition to neutralizing the alkaline effect of the carbonate, the acids served as a valuable source of phosphorus and sulfur.

This block was prepared using the apparatus described in Example I. The acids were first added to the FACW and mixed. Following the addition of the acid, the temperature of the mixture rose from 23° C. to 48° C. The $CaCO_3$ was next added slowly to the warm FACW-acid mixture over a period of about 15 to 20 minutes. Extensive foaming, resulting from the production of carbon dioxide, was observed during and following the addition of $CaCO_3$. Slow addition was used to control the neutralization reaction and prevent excessive foaming. After carbonate addition was completed, the blend continued to produce gas slowly for periods exceeding one hour.

After one hour, cooling was initiated. The liquid began to thicken when a temperature of about 27° C. was attained, and it was immediately poured into the mold.

Carbon dioxide production continued after the thickened liquid was transferred to the molds, and the solidifying product expanded as the evolved gases were entrapped. The volume of the dried block was about 50% larger than the freshly poured product. The product solidified in about six hours and attained maximum hardness after several days of curing.

The finished block was chemically analyzed and found to contain the following:

| Constituent | Percent |
|---|---|
| CPE | 31.9 |
| CPE from non-protein nitrogen | 27.5 |
| Lactic acid | 26.2 |
| Estimated solids | 70.5 |
| pH | 5.70 |
| Calcium | 6.42 |
| Phosphorus | 4.85 |
| Sulfur | 0.52 |

EXAMPLE IV

A 30-pound range block similar to that described in Example III was produced, with the inclusion of low moisture shelled corn, using the following formula:

| Ingredient | Percent |
|---|---|
| FACW (60% solids) | 52.2 |
| $CaCO_3$ | 12.0 |
| 85% $H_3PO_4$ | 12.0 |
| 95% $H_2SO_4$ | 1.6 |
| Ground corn, LMS | 20.0 |
| | 100 |

The procedure implemented was similar to that described in Example III. The corn fraction was added to the other premixed ingredients just prior to initiating the cooling operation. A temperature rise of 22° C. was observed during preparation of the premix. Solidification was initiated after cooling to approximately 32° C. The thickening product was not poured until it had attained a consistency that would permit suspension of the corn fragments. The solidification was completed after about 6 hours and maximum hardness was attained after several days of curing. The block matter was physically similar to that produced in Example III, and the corn particles appeared to be uniformly distributed within the product.

The finished product was observed to contain the following:

| Constituent | Percent |
|---|---|
| CPE | 28.5 |
| CPE from non-protein nitrogen | 22.6 |
| Lactic acid | 22.3 |
| Estimated solids | 74.0 |
| pH | 5.51 |
| Calcium | 4.50 |
| Phosphorus | 4.43 |
| Sulfur | 0.26 |

EXAMPLE V

A 200-gram high soy range cube was produced with FACW plus calcium serving as the binding agent using the following formulation:

| Ingredient | Percent |
|---|---|
| Soybean meal | 65.7 |
| FACW (60% solids) | 28.1 |
| $CaCl_2 \cdot 2H_2O$ | 6.2 |
|  | 100 |

The FACW and $CaCl_2$ ingredients were premixed with vigorous mechanical agitation for about 5 minutes. This premix was then blended with the soybean meal in a 500-liter stainless steel beaker using a large metal spatula. Blending was conducted for 3 to 5 minutes (just long enough to attain mixture uniformity) and immediately transferred to a 400-ml plastic beaker which served as a solidification mold. The blend was tightly packed by hand pressure, covered with plastic film and permitted to remain undisturbed for several hours before removing the mold. The mixing and packing operation employed in this example was sufficiently rapid to avoid premature solidification. The product was sufficiently moist and sticky at the time of packing to attain good binding.

The finished product was dry, observed to be of a desired hardness, and displayed good weathering characteristics. The finished product was estimated to contain the following:

| Constituent | Percent |
|---|---|
| CPE | 42.5 |
| CPE from non-protein nitrogen | 9.9 |
| Lactic acid | 10.1 |
| Estimated solids | 80.1 |
| Calcium | 1.90 |

EXAMPLE VI

A 200-gram soy range cube similar to that described in Example V was prepared with the inclusion of black strap molasses, using the following formula:

| Ingredient | Percent |
|---|---|
| Soybean Meal | 59.1 |
| FACW (60% solids) | 25.3 |
| Molasses, Black Strap | 10.0 |
| $CaCl_2 \cdot 2H_2O$ | 5.6 |
|  | 100 |

The preparation of this cube was similar to that produced in Example V. The molasses was premixed with the FACW prior to the addition of the calcium salts. This product was also dry, observed to display desired hardness and had good weathering characteristics. The finished product was to contain the following:

| Constituent | Percent |
|---|---|
| CPE | 38.5 |
| CPE from non-protein nitrogen | 8.91 |
| Lactic acid | 9.11 |
| Estimated solids | 81.8 |
| Calcium | 1.80 |

EXAMPLE VII

Range blocks similar in composition to commercially produced protein blocks were produced using FACW and $CaCl_2$ as binding agents in the following three formulations:

| INGREDIENTS | Percent | | |
|---|---|---|---|
|  | BLOCK 1 | BLOCK 2 | BLOCK 3 |
| Soybean oil meal | 47.9 | 40.4 | 30.3 |
| FACW | 26.7 | 32.8 | 41.1 |
| Dehydrated alfalfa | 9.20 | 9.20 | 9.20 |
| Linseed meal | 1.83 | 1.83 | 1.83 |
| Calcium chloride, dihydrate | 5.85 | 7.20 | 9.00 |
| Ammonium polyphosphate | 3.11 | 3.11 | 3.11 |
| Ammonium sulfate | 0.548 | 0.548 | 0.548 |
| Sodium chloride | 4.57 | 4.57 | 4.57 |
| Zinc sulfate, heptahydrate | 0.124 | 0.124 | 0.124 |
| Manganese sulfate, monohydrate | .0496 | .0496 | .0496 |
| Ferric sulfate | .0578 | .0578 | .0578 |
| Magnesium sulfate, dihydrate | 0.122 | 0.122 | 0.122 |
| Cupric sulfate | .0952 | .0952 | .0952 |
| Cobalt sulfate | .00194 | .00194 | .00194 |
| Sodium iodide | .00066 | .00066 | .00066 |
| Vitamins | # | # | # |
| TOTAL | 100 | 100 | 400 |

50,000 and 12,500 U.S.P. units of Vitamin A and Vitamin $D_3$, respectively, added per pound of block.

The FACW and $CaCl_2$ components were premixed and added collectively to the remaining dry ingredients, which were also premixed. The FACW-$CaCl_2$ premixes were prepared in a 2-gallon plastic bucket. Each FACW fraction was blended vigorously with a Grohav ® air mixer fitted with a single set of 2-inch blades during the slow addition of each respective $CaCl_2$ fraction. Rapid mixing and slow addition was used to prevent agglomeration and clumping of the $CaCl_2$. Each FACW-calcium premix was mixed for about five minutes after the addition to assure that $CaCl_2$ had been totally dissolved. The temperature of each FACW fraction was elevated during the premixing operations in which $CaCl_2$ was added. The temperature of the premixes were elevated about 20° C. with the 22% additions of $CaCl_2 \cdot 2H_2O$.

The premixing of the dry ingredients was conducted in a Davis batch horizontal ribbon-type mixer (Model #S-1) with a mixing capacity of five cubic feet. The liquid premix was poured slowly and uniformly onto the mixing dry ingredients to help assure uniformity of mix. After the liquid addition was completed, the mixing was continued for an additional five minutes. Any feed that was sticking in excess to the ribbon blades or remaining stagnant in the lower corners of the mixer was then removed with a metal spatula and mixing was continued for an additional five minutes.

Each of the blendings of feed ingredients mixed loosely and freely in the horizontal ribbon mixer. The mixtures prepared to produce blocks 1 and 2 (27 and 33% FACW, respectively) were moist and slightly sticky. The block 3 mixture (41% FACW) was noticeably more moist and sticky. Before solidification, the block 3 mixture was wet and almost paste-like. Even though the three mixtures blended uniformly without clumping, they were observed to pack tightly if compressed in one's hand.

Excessive mixing times had to be avoided, since solidification of the feed mixes initiated in about 15 minutes or less. If not removed from the mixer expeditiously, the mixtures were observed to form a hard, relatively dry crust on the back side of the ribbon blades and on the mixer walls in areas of stagnant mixing. Also, if mixed excessively, the feed mixtures were observed to dry to an extent that did not permit adequate packing, i.e., the feed particles lost their adhesive nature.

The moist, freshly-prepared feed blends were easily packed with good uniformity into the block mold. Some disuniformity was observed in the density of the pack due to the layered addition of the feed mixture, i.e., the top portion of each strata was observed to be slightly more dense than the bottom portion. The moist feed materials prepared to produce blocks 1 and 2 compressed to very firm solid masses that were not easily crumbled. The block 3 mixture remained somewhat soft and pasty immediately after packing.

The feed mixtures were removed immediately from the mixer and packed into a block solidification mold. The mold was a rectangular wooden box, constructed to approximate the shape and size of most commercial range blocks. The faces of the mold were held together by screws so as to permit the disassemblement of the box for easy removal of the finished block. The open end from which the mold was filled was filled with a movable lid that fit within the box. After filling, a 25-pound weight was placed on the movable lid so as to apply a constant pressure to the solidifying feed mixture.

Each feed mixture was packed manually in the solidification mold with the butt end of a 4-foot length of 4×4" board weighing approximately ten pounds. The wet feed was added to the box in fractions weighing 1–2 pounds each with each fraction being thoroughly tamped (packed) before the addition of each subsequent fraction. Once the mold was filled, the lid was placed on the exposed feed surface and weighed.

Even though the feed blends were left in the mold for 4 to 6 hours, it appears that blocks 1 and 2 would retain their shape and remain firm if the mold was removed immediately after packing. The blocks would likely maintain some surface stickiness but would probably be resistant to crumbling and breakage. After being compressed into the form of a block, they could be immediately packaged and stacked without being damaged.

The mold was removed from block 1 with little difficulty. The mold was easily freed from the block mass with little resistance and little feed remained adhered to the wood. The block surface was dry and firm. The mold, however, was not easily removed from blocks 2 and 3. Considerable force was needed to pull away from the wooden mold from block 2. Large fragments of the hardened feed adhered to the wood and were torn from the block. The block surface was still sticky but remained firm. This problem possibly could have been alleviated if the mold were lined with sheet plastic or other non-stick surface prior to filling. Block 3 adhered even more firmly to the wood mold. A metal spatula had to be forced between the block and the mold to release it. The block surface remained very sticky and although it was firm, an impression could be made in it with the force of a person's thumb.

After being bagged and allowed to stand for a one-week curing period, all of the blocks were very hard and dry and displayed no surface stickiness. The blocks as a whole were not easily crumbled, but some crumbling was observed at the edges of the block surfaces.

Chemical analysis of the blocks provided the following information:

| NUTRIENT | Block 1 | Block 2 | Block 3 |
| --- | --- | --- | --- |
| % Crude protein equivalent | 39.5 | 38.1 | 36.3 |
| % CPE derived from NPN | 12.4 | 15.4 | 17.7 |
| % Lactic acid | 10.5 | 12.8 | 17.6 |
| % Drymatter | 83.8 | 81.7 | 78.3 |
| pH | 5.68 | 5.64 | 5.57 |
| % Ash | 12.1 | 12.8 | 15.4 |
| % Calcium | 1.64 | 2.13 | 2.37 |
| % Phosphorus | 0.91 | 0.69 | 0.71 |
| % Sulfur | 0.07 | 0.10 | 0.18 |
| % Sodium | 1.58 | 1.41 | 1.98 |
| % Chloride | 7.8 | 10 | 11 |

The blocks were fed and consumed by cattle in approximately the correct amount for their size and basal ration. These blocks weathered well and were judged to be equivalent to normal feed blocks.

This process is not restricted to these examples or devices but could be carried out using commercially available food and feed industry equipment by control of temperatures, FACW level and calcium level. The molds used could be any commercially available container provided it was sufficiently rigid. Pressing of the material into the mold could be by any device such as cheese block presses or other such commonly used device. Feed block presses could also be used but high pressure is not required.

What is claimed is:

1. A method of producing a ruminant feed containing solidified fermented ammoniated condensed whey which method consists essentially of mixing fermented ammoniated condensed whey containing 35–55% ammonium lactate with an effective amount of a calcium salt of a strong mineral acid selected from the group consisting of calcium chloride, calcium sulfate and calcium phosphate to cause the solidification of said fermented ammoniated condensed whey, and allowing the resulting mixture to stand until it has solidified.

2. A method as set forth in claim 1 in which said salt is calcium chloride.

3. A method as set forth in claim 1 in which the amount of calcium salt added is sufficient to provide 6–10% calcium, based on the weight of fermented ammoniated condensed whey.

4. A method as set forth in claim 1 in which the mixture is solidified in a mold to produce a protein supplement lick block.

5. A method as set forth in claim 1 including the step of mixing said mixture with forage, roughage or other plant products suitable for ruminant feeding, whereby solidified fermented ammoniated condensed whey functions as a binder for said plant material.

6. A method as set forth in claim 1 including maintaining said mixture above a temperature at which it can solidify, placing said mixture in a solidification mold while it is above said temperature, and then allowing said mixture to cool.

7. A method as set forth in claim 1 including extruding said mixture before it solidifies.

8. A method of producing a ruminant feed containing solidified fermented ammoniated condensed whey which method consists essentially of mixing fermented ammoniated condensed whey with an alkaline calcium compound which is reactive with a strong mineral acid to form a calcium salt of said strong mineral acid, adding a strong mineral acid selected from the group consisting of hydrochloric acid, sulfuric acid and phosphoric acid to react with said compound to form said calcium salt, the amount of said calcium salt formed being effective to cause solidification of said fermented ammoniated condensed whey, and allowing the resulting mixture to stand until it has solidified.

9. A method as set forth in claim 8 in which said calcium compound is selected from the group consisting of calcium carbonate, calcium oxide and calcium hydroxide.

10. A method as set forth in claim 8 in which the amount of calcium compound added is sufficient to provide 6–10% calcium, based on the weight of fermented ammoniated condensed whey.

11. A method as set forth in claim 8 in which the mixture is solidified in a mold to produce a protein supplement lick block.

12. A method as set forth in claim 8 including the step of mixing said mixture with forage, roughage or other plant products suitable for ruminant feeding, whereby solidified fermented ammoniated condensed whey functions as a binder for said plant material.

13. A method as set forth in claim 8 including maintaining said mixture above a temperature at which it can solidify, and placing said mixture in a solidification mold while it is above said temperature.

14. A method as set forth in claim 8 including extruding said mixture before it solidifies.

* * * * *